(12) United States Patent
Brown et al.

(10) Patent No.: US 7,523,667 B2
(45) Date of Patent: Apr. 28, 2009

(54) DIAGNOSTICS OF IMPULSE PIPING IN AN INDUSTRIAL PROCESS

(75) Inventors: Gregory C. Brown, Chanhassen, MN (US); Mark S. Schumacher, Minneapolis, MN (US)

(73) Assignee: Rosemount Inc., Eden Prairie, MN (US)

( * ) Notice: Subject to any disclaimer, the term of this patent is extended or adjusted under 35 U.S.C. 154(b) by 0 days.

(21) Appl. No.: 10/744,809

(22) Filed: Dec. 23, 2003

(65) Prior Publication Data

US 2005/0132808 A1 Jun. 23, 2005

(51) Int. Cl.
*G01N 29/00* (2006.01)

(52) U.S. Cl. .............................. 73/592; 73/611; 73/622; 73/40.5

(58) Field of Classification Search .................. 73/592, 73/644, 861.23, 1.16, 861.355, 861.356, 73/861.357, 861.22, 40.5 A, 40.5 R, 40.5, 73/611; 702/104–105, 45, 183, 55, 69, 191, 702/195; 340/606

See application file for complete search history.

(56) References Cited

U.S. PATENT DOCUMENTS

| | | | |
|---|---|---|---|
| 3,096,434 A | 7/1963 | King | 235/151 |
| 3,404,264 A | 10/1968 | Kugler | 235/194 |
| 3,468,164 A | 9/1969 | Sutherland | 73/343 |
| 3,590,370 A | 6/1971 | Fleischer | 324/51 |
| 3,618,592 A | 11/1971 | Stewart | 128/2.05 R |
| 3,688,190 A | 8/1972 | Blum | 324/61 R |
| 3,691,842 A | 9/1972 | Akeley | 73/398 C |
| 3,701,280 A | 10/1972 | Stroman | 73/194 |
| 3,849,637 A | 11/1974 | Caruso et al. | 235/151 |
| 3,855,858 A | 12/1974 | Cushing | 73/194 EM |
| 3,948,098 A | 4/1976 | Richardson et al. | 73/861.24 |
| 3,952,759 A | 4/1976 | Ottenstein | 137/12 |
| 3,964,296 A | 6/1976 | Matzuk | 73/67.5 |
| 3,973,184 A | 8/1976 | Raber | 324/51 |
| RE29,383 E | 9/1977 | Gallatin et al. | 137/14 |
| 4,058,975 A | 11/1977 | Gilbert et al. | 60/39.28 |
| 4,083,031 A * | 4/1978 | Pharo, Jr. | 367/135 |
| 4,099,413 A | 7/1978 | Ohte et al. | 73/359 |
| 4,102,199 A | 7/1978 | Talpouras | 73/362 |
| 4,122,719 A | 10/1978 | Carlson et al. | 73/342 |

(Continued)

FOREIGN PATENT DOCUMENTS

CA 999950 11/1976

(Continued)

OTHER PUBLICATIONS

"Notification of Transmittal of The International Search Report or the Declaration", PCT/US2004/025291.

(Continued)

*Primary Examiner*—Hezron E. Williams
*Assistant Examiner*—Jacques M. Saint-Surin
(74) *Attorney, Agent, or Firm*—Westman, Champlin & Kelly, P.A.

(57) ABSTRACT

Diagnosing operation of an impulse piping line in an industrial process is provided. A vibration source transmits a vibration signal through the piping and a vibration signal receiver receives the vibration signal. The operation of the impulse piping line is diagnosed, such as failure or impending failures, based upon the received vibration signal.

41 Claims, 3 Drawing Sheets

U.S. PATENT DOCUMENTS

| | | | | |
|---|---|---|---|---|
| 4,249,164 A | | 2/1981 | Tivy | 340/870.3 |
| 4,250,490 A | | 2/1981 | Dahlke | 340/870.37 |
| 4,255,964 A | * | 3/1981 | Morison | 73/24.01 |
| 4,279,013 A | | 7/1981 | Cameron et al. | 340/870.37 |
| 4,337,516 A | | 6/1982 | Murphy et al. | 364/551 |
| 4,355,536 A | | 10/1982 | McShane et al. | 73/633 |
| 4,383,443 A | * | 5/1983 | Langdon | 73/290 V |
| 4,393,711 A | | 7/1983 | Lapides | 73/592 |
| 4,399,824 A | | 8/1983 | Davidson | 128/736 |
| 4,417,312 A | | 11/1983 | Cronin et al. | 364/510 |
| 4,423,634 A | * | 1/1984 | Audenard et al. | 73/587 |
| 4,448,062 A | | 5/1984 | Peterson et al. | 73/86 |
| 4,459,858 A | | 7/1984 | Marsh | 73/861.12 |
| 4,463,612 A | | 8/1984 | Thompson | 73/861.22 |
| 4,517,468 A | | 5/1985 | Kemper et al. | 290/52 |
| 4,528,869 A | | 7/1985 | Kubo et al. | 74/695 |
| 4,530,234 A | | 7/1985 | Cullick et al. | 73/53 |
| 4,536,753 A | | 8/1985 | Parker | 340/566 |
| 4,540,468 A | | 9/1985 | Genco et al. | 162/49 |
| 4,571,689 A | | 2/1986 | Hildebrand et al. | 364/481 |
| 4,630,265 A | | 12/1986 | Sexton | 370/85 |
| 4,635,214 A | | 1/1987 | Kasai et al. | 364/551 |
| 4,641,529 A | | 2/1987 | Lorenzi et al. | 73/601 |
| 4,642,782 A | | 2/1987 | Kemper et al. | 364/550 |
| 4,644,479 A | | 2/1987 | Kemper et al. | 364/550 |
| 4,649,515 A | | 3/1987 | Thompson et al. | 364/900 |
| 4,668,473 A | | 5/1987 | Agarwal | 422/62 |
| 4,686,638 A | | 8/1987 | Furuse | 364/558 |
| 4,696,191 A | * | 9/1987 | Claytor et al. | 73/600 |
| 4,707,796 A | | 11/1987 | Calabro et al. | 364/552 |
| 4,720,806 A | | 1/1988 | Schippers et al. | 364/551 |
| 4,736,367 A | | 4/1988 | Wroblewski et al. | 370/85 |
| 4,736,763 A | | 4/1988 | Britton et al. | 137/10 |
| 4,758,308 A | | 7/1988 | Carr | 162/263 |
| 4,777,585 A | | 10/1988 | Kokawa et al. | 364/164 |
| 4,807,151 A | | 2/1989 | Citron | 364/510 |
| 4,818,994 A | | 4/1989 | Orth et al. | 340/501 |
| 4,831,564 A | | 5/1989 | Suga | 364/551.01 |
| 4,833,922 A | | 5/1989 | Frick et al. | 73/756 |
| 4,841,286 A | | 6/1989 | Kummer | 340/653 |
| 4,853,693 A | | 8/1989 | Eaton-Williams | 340/588 |
| 4,873,655 A | | 10/1989 | Kondraske | 364/553 |
| 4,907,167 A | | 3/1990 | Skeirik | 364/500 |
| 4,924,418 A | | 5/1990 | Backman et al. | 364/550 |
| 4,926,364 A | | 5/1990 | Brotherton | 364/581 |
| 4,934,196 A | | 6/1990 | Romano | 73/861.38 |
| 4,939,753 A | | 7/1990 | Olson | 375/107 |
| 4,964,125 A | | 10/1990 | Kim | 371/15.1 |
| 4,988,990 A | | 1/1991 | Warrior | 340/25.5 |
| 4,992,965 A | | 2/1991 | Holter et al. | 364/551.01 |
| 5,005,142 A | | 4/1991 | Lipchak et al. | 364/550 |
| 5,014,543 A | | 5/1991 | Franklin et al. | 73/40.5 |
| 5,019,760 A | | 5/1991 | Chu et al. | 318/490 |
| 5,025,344 A | | 6/1991 | Maly et al. | 361/88 |
| 5,043,862 A | | 8/1991 | Takahashi et al. | 364/162 |
| 5,047,990 A | * | 9/1991 | Gafos et al. | 367/6 |
| 5,053,815 A | | 10/1991 | Wendell | 355/208 |
| 5,057,774 A | | 10/1991 | Verhelst et al. | 324/537 |
| 5,067,099 A | | 11/1991 | McCown et al. | 364/550 |
| 5,081,598 A | | 1/1992 | Bellows et al. | 364/550 |
| 5,089,979 A | | 2/1992 | McEachern et al. | 364/571.04 |
| 5,089,984 A | | 2/1992 | Struger et al. | 395/650 |
| 5,094,109 A | | 3/1992 | Dean et al. | 73/718 |
| 5,098,197 A | | 3/1992 | Shepard et al. | 374/120 |
| 5,099,436 A | | 3/1992 | McCown et al. | 364/550 |
| 5,103,409 A | | 4/1992 | Shimizu et al. | 364/556 |
| 5,111,531 A | | 5/1992 | Grayson et al. | 395/23 |
| 5,121,467 A | | 6/1992 | Skeirik | 395/11 |
| 5,122,794 A | | 6/1992 | Warrior | 340/825.2 |
| 5,122,976 A | | 6/1992 | Bellows et al. | 364/550 |
| 5,130,936 A | | 7/1992 | Sheppard et al. | 364/551.01 |
| 5,134,574 A | | 7/1992 | Beaverstock et al. | 364/551.01 |
| 5,137,370 A | | 8/1992 | McCullock et al. | 374/173 |
| 5,142,612 A | | 8/1992 | Skeirik | 395/11 |
| 5,143,452 A | | 9/1992 | Maxedon et al. | 374/170 |
| 5,148,378 A | | 9/1992 | Shibayama et al. | 364/551.07 |
| 5,150,289 A | | 9/1992 | Badavas | 364/154 |
| 5,167,009 A | | 11/1992 | Skeirik | 395/27 |
| 5,175,678 A | | 12/1992 | Frerichs et al. | 364/148 |
| 5,193,143 A | | 3/1993 | Kaemmerer et al. | 395/51 |
| 5,197,114 A | | 3/1993 | Skeirik | 395/22 |
| 5,197,328 A | | 3/1993 | Fitzgerald | 73/168 |
| 5,212,765 A | | 5/1993 | Skeirik | 395/11 |
| 5,214,582 A | | 5/1993 | Gray | 364/424.03 |
| 5,216,226 A | | 6/1993 | Miyoshi | 219/497 |
| 5,224,203 A | | 6/1993 | Skeirik | 395/22 |
| 5,228,780 A | | 7/1993 | Shepard et al. | 374/175 |
| 5,235,527 A | | 8/1993 | Ogawa et al. | 364/571.05 |
| 5,265,031 A | | 11/1993 | Malczewski | 364/497 |
| 5,265,222 A | | 11/1993 | Nishiya et al. | 395/3 |
| 5,269,311 A | | 12/1993 | Kirchner et al. | 128/672 |
| 5,274,572 A | | 12/1993 | O'Neill et al. | 364/550 |
| 5,282,131 A | | 1/1994 | Rudd et al. | 364/164 |
| 5,282,261 A | | 1/1994 | Skeirik | 395/22 |
| 5,293,585 A | | 3/1994 | Morita | 395/52 |
| 5,303,181 A | | 4/1994 | Stockton | 365/96 |
| 5,305,230 A | | 4/1994 | Matsumoto et al. | 364/495 |
| 5,311,421 A | | 5/1994 | Nomura et al. | 364/157 |
| 5,317,520 A | | 5/1994 | Castle | 364/482 |
| 5,327,357 A | | 7/1994 | Feinstein et al. | 364/502 |
| 5,333,240 A | | 7/1994 | Matsumoto et al. | 395/23 |
| 5,340,271 A | | 8/1994 | Freeman et al. | 415/1 |
| 5,347,843 A | | 9/1994 | Orr et al. | 73/3 |
| 5,349,541 A | | 9/1994 | Alexandro, Jr. et al. | 364/578 |
| 5,357,449 A | | 10/1994 | Oh | 364/551.01 |
| 5,361,628 A | | 11/1994 | Marko et al. | 73/116 |
| 5,365,423 A | | 11/1994 | Chand | 364/140 |
| 5,365,787 A | | 11/1994 | Hernandez et al. | 73/660 |
| 5,367,612 A | | 11/1994 | Bozich et al. | 395/22 |
| 5,369,674 A | * | 11/1994 | Yokose et al. | 376/245 |
| 5,384,699 A | | 1/1995 | Levy et al. | 364/413.13 |
| 5,386,373 A | | 1/1995 | Keeler et al. | 364/577 |
| 5,388,465 A | | 2/1995 | Okaniwa et al. | 73/861.17 |
| 5,392,293 A | | 2/1995 | Hsue | 324/765 |
| 5,394,341 A | | 2/1995 | Kepner | 364/551.01 |
| 5,394,543 A | | 2/1995 | Hill et al. | 395/575 |
| 5,404,064 A | | 4/1995 | Mermelstein et al. | 310/319 |
| 5,408,406 A | | 4/1995 | Mathur et al. | 364/163 |
| 5,408,586 A | | 4/1995 | Skeirik | 395/23 |
| 5,410,495 A | | 4/1995 | Ramamurthi | 364/511.05 |
| 5,414,645 A | | 5/1995 | Hirano | 364/551.01 |
| 5,419,197 A | | 5/1995 | Ogi et al. | 73/659 |
| 5,430,642 A | | 7/1995 | Nakajima et al. | 364/148 |
| 5,434,774 A | | 7/1995 | Seberger | 364/172 |
| 5,436,705 A | | 7/1995 | Raj | 355/246 |
| 5,440,478 A | | 8/1995 | Fisher et al. | 364/188 |
| 5,442,639 A | | 8/1995 | Crowder et al. | 371/20.1 |
| 5,467,355 A | | 11/1995 | Umeda et al. | 364/571.04 |
| 5,469,070 A | | 11/1995 | Koluvek | 324/713 |
| 5,469,156 A | | 11/1995 | Kogura | 340/870.38 |
| 5,469,735 A | | 11/1995 | Watanabe | 73/118.1 |
| 5,469,749 A | | 11/1995 | Shimada et al. | 73/861.47 |
| 5,481,199 A | | 1/1996 | Anderson et al. | 324/705 |
| 5,481,200 A | | 1/1996 | Voegele et al. | 324/718 |
| 5,483,387 A | | 1/1996 | Bauhahn et al. | 359/885 |
| 5,485,753 A | | 1/1996 | Burns et al. | 73/720 |
| 5,486,996 A | | 1/1996 | Samad et al. | 364/152 |
| 5,488,697 A | | 1/1996 | Kaemmerer et al. | 395/51 |
| 5,489,831 A | | 2/1996 | Harris | 318/701 |
| 5,495,769 A | | 3/1996 | Broden et al. | 73/718 |
| 5,497,661 A | | 3/1996 | Stripf et al. | 73/611 |
| 5,510,779 A | | 4/1996 | Maltby et al. | 340/870.3 |
| 5,511,004 A | | 4/1996 | Dubost et al. | 364/551.01 |
| 5,521,840 A | | 5/1996 | Bednar | 364/508 |

| | | | |
|---|---|---|---|
| 5,526,293 A | 6/1996 | Mozumder et al. ............. 364/578 |
| 5,539,638 A | 7/1996 | Keeler et al. ............. 364/424.03 |
| 5,548,528 A | 8/1996 | Keeler et al. ................. 364/497 |
| 5,555,190 A | 9/1996 | Derby et al. ................. 364/510 |
| 5,560,246 A | 10/1996 | Bottinger et al. ........... 73/861.15 |
| 5,561,599 A | 10/1996 | Lu ................................. 364/164 |
| 5,570,034 A | 10/1996 | Needham et al. ............. 324/763 |
| 5,570,300 A | 10/1996 | Henry et al. ............. 364/551.01 |
| 5,572,420 A | 11/1996 | Lu ................................. 364/153 |
| 5,573,032 A | 11/1996 | Lenz et al. ..................... 137/486 |
| 5,578,763 A | 11/1996 | Spencer et al. ............ 73/861.08 |
| 5,591,922 A | 1/1997 | Segeral et al. ............... 73/861.04 |
| 5,598,521 A | 1/1997 | Kilgore et al. ................. 395/326 |
| 5,600,148 A | 2/1997 | Cole et al. ................... 250/495.1 |
| 5,608,650 A | 3/1997 | McClendon et al. ........ 364/510 |
| 5,623,605 A | 4/1997 | Keshav et al. ........... 395/200.17 |
| 5,629,870 A | 5/1997 | Farag et al. ............. 364/551.01 |
| 5,633,809 A | 5/1997 | Wissenbach et al. ........ 364/510 |
| 5,637,802 A | 6/1997 | Frick et al. ..................... 73/724 |
| 5,640,491 A | 6/1997 | Bhat et al. ....................... 395/22 |
| 5,644,240 A | 7/1997 | Brugger ......................... 324/439 |
| 5,650,943 A | 7/1997 | Powell et al. ................. 364/550 |
| 5,654,869 A | 8/1997 | Ohi et al. ........................ 361/540 |
| 5,661,668 A | 8/1997 | Yemini et al. ................. 364/550 |
| 5,665,899 A | 9/1997 | Willcox ............................ 73/1.63 |
| 5,668,322 A | 9/1997 | Broden ............................. 73/756 |
| 5,669,713 A | 9/1997 | Schwartz et al. ................. 374/1 |
| 5,671,335 A | 9/1997 | Davis et al. ...................... 395/23 |
| 5,672,247 A | 9/1997 | Pangalos et al. ............... 162/65 |
| 5,675,504 A | 10/1997 | Serodes et al. ............... 364/496 |
| 5,675,724 A | 10/1997 | Beal et al. ................. 395/182.02 |
| 5,680,109 A | 10/1997 | Lowe et al. ................... 340/608 |
| 5,682,317 A | 10/1997 | Keeler et al. ............. 364/431.03 |
| 5,700,090 A | 12/1997 | Eryurek ......................... 374/210 |
| 5,703,575 A | 12/1997 | Kirpatrick ................. 340/870.17 |
| 5,704,011 A | 12/1997 | Hansen et al. .................. 395/22 |
| 5,705,754 A | 1/1998 | Keita et al. ................. 73/861.354 |
| 5,705,978 A | 1/1998 | Frick et al. ..................... 340/511 |
| 5,708,211 A | 1/1998 | Jepson et al. .............. 73/861.04 |
| 5,708,585 A | 1/1998 | Kushion .................. 364/431.061 |
| 5,710,370 A | 1/1998 | Shanahan et al. ............. 73/1.35 |
| 5,710,708 A | 1/1998 | Wiegand .................... 364/470.1 |
| 5,713,668 A | 2/1998 | Lunghofer et al. ........... 374/179 |
| 5,719,378 A | 2/1998 | Jackson, Jr. et al. ......... 219/497 |
| 5,736,649 A | 4/1998 | Kawasaki et al. ......... 73/861.23 |
| 5,741,074 A | 4/1998 | Wang et al. ................... 374/185 |
| 5,742,845 A | 4/1998 | Wagner ......................... 395/831 |
| 5,746,511 A | 5/1998 | Eryurek et al. ................... 374/2 |
| 5,747,701 A | 5/1998 | Marsh et al. ............... 73/861.23 |
| 5,752,008 A | 5/1998 | Bowling ....................... 395/500 |
| 5,756,898 A | 5/1998 | Diatschenko et al. ........ 73/592 |
| 5,764,539 A | 6/1998 | Rani ............................... 364/557 |
| 5,764,891 A | 6/1998 | Warrior .................... 395/200.2 |
| 5,781,024 A | 7/1998 | Blomberg et al. ............. 324/763 |
| 5,781,878 A | 7/1998 | Mizoguchi et al. ........... 701/109 |
| 5,790,413 A | 8/1998 | Bartusiak et al. .............. 364/485 |
| 5,801,689 A | 9/1998 | Huntsman .................... 345/329 |
| 5,805,442 A | 9/1998 | Crater et al. ................... 364/138 |
| 5,817,950 A | 10/1998 | Wiklund et al. ........... 73/861.66 |
| 5,825,664 A | 10/1998 | Warrior et al. .................. 700/7 |
| 5,828,567 A | 10/1998 | Eryurek et al. ................ 700/79 |
| 5,829,876 A | 11/1998 | Schwartz et al. ................. 374/1 |
| 5,848,383 A | 12/1998 | Yuuns ............................. 702/102 |
| 5,854,993 A | 12/1998 | Crichnik ......................... 702/54 |
| 5,859,964 A | 1/1999 | Wang et al. ............... 395/185.1 |
| 5,869,772 A | 2/1999 | Storer ....................... 73/861.24 |
| 5,874,676 A | 2/1999 | Maki, Jr. ........................ 73/579 |
| 5,876,122 A | 3/1999 | Eryurek ......................... 374/183 |
| 5,880,376 A | 3/1999 | Sai et al. ..................... 73/861.08 |
| 5,887,978 A | 3/1999 | Lunghofer et al. ........... 374/179 |
| 5,908,990 A | 6/1999 | Cummings ................. 73/861.22 |
| 5,920,016 A | 7/1999 | Broden ............................ 73/756 |
| 5,923,557 A | 7/1999 | Eidson ..................... 364/471.03 |
| 5,924,086 A | 7/1999 | Mathur et al. ................... 706/25 |
| 5,926,778 A | 7/1999 | Pöppel .......................... 702/130 |
| 5,934,371 A | 8/1999 | Bussear et al. .................. 166/53 |
| 5,936,514 A | 8/1999 | Anderson et al. ........ 340/310.01 |
| 5,940,290 A | 8/1999 | Dixon ........................... 364/138 |
| 5,956,663 A | 9/1999 | Eryurek et al. ................ 702/183 |
| 5,970,430 A | 10/1999 | Burns et al. ................... 702/122 |
| 6,002,952 A | 12/1999 | Diab et al. .................... 600/310 |
| 6,014,612 A | 1/2000 | Larson et al. ................. 702/183 |
| 6,014,902 A | 1/2000 | Lewis et al. ................. 73/861.12 |
| 6,016,523 A | 1/2000 | Zimmerman et al. .......... 710/63 |
| 6,016,706 A | 1/2000 | Yamamoto et al. .................. 9/6 |
| 6,017,143 A | 1/2000 | Eryurek et al. ................. 700/51 |
| 6,023,399 A | 2/2000 | Kogure ........................... 361/23 |
| 6,026,352 A | 2/2000 | Burns et al. ................... 702/182 |
| 6,038,579 A | 3/2000 | Sekine ........................... 708/400 |
| 6,045,260 A | 4/2000 | Schwartz et al. ............. 374/183 |
| 6,046,642 A | 4/2000 | Brayton et al. ............... 330/296 |
| 6,047,220 A | 4/2000 | Eryurek et al. .................. 700/28 |
| 6,047,222 A | 4/2000 | Burns et al. ..................... 700/79 |
| 6,052,655 A | 4/2000 | Kobayashi et al. ........... 702/184 |
| 6,059,254 A | 5/2000 | Sundet et al. ................. 248/678 |
| 6,061,603 A | 5/2000 | Papadopoulos et al. ....... 700/83 |
| 6,072,150 A | 6/2000 | Sheffer .................... 219/121.83 |
| 6,094,600 A | 7/2000 | Sharpe, Jr. et al. ............ 700/19 |
| 6,112,131 A | 8/2000 | Ghorashi et al. ............. 700/142 |
| 6,119,047 A * | 9/2000 | Eryurek et al. .................. 700/28 |
| 6,119,529 A | 9/2000 | Di Marco et al. ......... 73/861.68 |
| 6,139,180 A | 10/2000 | Usher et al. ...................... 374/1 |
| 6,151,560 A | 11/2000 | Jones ............................. 702/58 |
| 6,179,964 B1 | 1/2001 | Begemann et al. ........... 162/198 |
| 6,182,501 B1 | 2/2001 | Furuse et al. ................. 73/49.2 |
| 6,192,281 B1 | 2/2001 | Brown et al. ...................... 700/2 |
| 6,195,591 B1 | 2/2001 | Nixon et al. ...................... 700/2 |
| 6,199,018 B1 * | 3/2001 | Quist et al. ..................... 702/34 |
| 6,209,048 B1 | 3/2001 | Wolff ............................. 710/62 |
| 6,236,948 B1 | 5/2001 | Eck et al. ........................ 702/45 |
| 6,237,424 B1 | 5/2001 | Salmasi et al. ............ 73/861.17 |
| 6,263,487 B1 | 7/2001 | Stripf et al. ...................... 717/1 |
| 6,272,438 B1 | 8/2001 | Cunningham et al. .......... 702/56 |
| 6,289,735 B1 | 9/2001 | Dister et al. .................... 73/579 |
| 6,298,377 B1 | 10/2001 | Hartikainen et al. ......... 709/223 |
| 6,307,483 B1 | 10/2001 | Westfield et al. ......... 340/870.11 |
| 6,311,136 B1 | 10/2001 | Henry et al. .................... 702/45 |
| 6,317,701 B1 | 11/2001 | Pyostsia et al. ................ 702/188 |
| 6,327,914 B1 | 12/2001 | Dutton .................... 73/861.356 |
| 6,347,252 B1 | 2/2002 | Behr et al. ........................ 700/2 |
| 6,356,191 B1 | 3/2002 | Kirkpatrick et al. .......... 340/501 |
| 6,360,277 B1 | 3/2002 | Ruckley et al. ................. 9/250 |
| 6,367,328 B1 | 4/2002 | Gorman et al. ................. 73/592 |
| 6,370,448 B1 | 4/2002 | Eryurek et al. ................ 700/282 |
| 6,377,859 B1 | 4/2002 | Brown et al. ..................... 700/79 |
| 6,378,364 B1 * | 4/2002 | Pelletier et al. ............. 73/152.47 |
| 6,396,426 B1 | 5/2002 | Balard et al. .................. 341/120 |
| 6,397,114 B1 | 5/2002 | Eryurek et al. ................. 700/51 |
| 6,405,099 B1 | 6/2002 | Nagai et al. .................... 700/159 |
| 6,425,038 B1 | 7/2002 | Sprecher ...................... 710/269 |
| 6,434,504 B1 | 8/2002 | Eryurek et al. ................ 702/130 |
| 6,449,574 B1 | 9/2002 | Eryurek et al. ................. 702/99 |
| 6,473,656 B1 | 10/2002 | Langels et al. ................. 700/17 |
| 6,473,710 B1 | 10/2002 | Eryurek ......................... 702/133 |
| 6,480,793 B1 | 11/2002 | Martin ........................... 702/45 |
| 6,492,921 B1 | 12/2002 | Kunitani et al. ............. 341/118 |
| 6,493,689 B2 | 12/2002 | Kotoulas et al. ............... 706/23 |
| 6,497,222 B2 * | 12/2002 | Bolz et al. .................... 123/479 |
| 6,505,517 B1 | 1/2003 | Eryurek et al. ............ 73/861.08 |
| 6,519,546 B1 | 2/2003 | Eryurek et al. ............... 702/130 |
| 6,532,392 B1 | 3/2003 | Eryurek et al. ................ 700/54 |
| 6,539,267 B1 | 3/2003 | Eryurek et al. ................ 700/51 |
| 6,546,814 B1 | 4/2003 | Choe et al. ................. 73/862.08 |
| 6,556,145 B1 | 4/2003 | Kirkpatrick et al. .... 340/870.17 |
| 6,561,038 B2 | 5/2003 | Gravel et al. .................. 73/729.2 |
| 6,567,006 B1 * | 5/2003 | Lander et al. ................. 340/605 |

| | | | | | | |
|---|---|---|---|---|---|---|
| 6,584,847 | B1 | 7/2003 | Hirose ............... 73/579 | EP | 0 807 804 A2 | 11/1997 |
| 6,594,603 | B1 | 7/2003 | Eryurek et al. ........ 702/104 | EP | 1 058 093 A1 | 5/1999 |
| 6,597,997 | B2 * | 7/2003 | Tingley ............... 702/34 | EP | 0 335 957 B1 | 11/1999 |
| 6,601,005 | B1 * | 7/2003 | Eryurek et al. ........ 702/104 | EP | 1 022 626 A2 | 7/2000 |
| 6,611,775 | B1 | 8/2003 | Coursolle et al. ........ 702/65 | FR | 2 302 514 | 9/1976 |
| 6,615,149 | B1 | 9/2003 | Wehrs ............... 702/76 | FR | 2 334 827 | 7/1977 |
| 6,654,697 | B1 | 11/2003 | Eryurek et al. ........ 702/47 | GB | 928704 | 6/1963 |
| 6,701,274 | B1 | 3/2004 | Eryurek et al. ........ 702/140 | GB | 1 534 280 | 11/1978 |
| 6,727,812 | B2 * | 4/2004 | Sauler et al. ........ 340/511 | GB | 1 534 288 | 11/1978 |
| 6,751,560 | B1 * | 6/2004 | Tingley et al. ........ 702/51 | GB | 2 310 346 A | 8/1997 |
| 6,758,168 | B2 | 7/2004 | Koskinen et al. ........ 122/7 | GB | 2 317 969 | 4/1998 |
| 6,813,588 | B1 | 11/2004 | Daugert et al. ........ 702/183 | GB | 2 342 453 A | 4/2000 |
| 7,010,459 | B2 | 3/2006 | Eryurek et al. ........ 702/182 | GB | 2 347 232 A | 8/2000 |
| 7,036,381 | B2 | 5/2006 | Broden et al. ........ 73/708 | JP | 56031573 | 3/1981 |
| 7,040,179 | B2 * | 5/2006 | Drahm et al. ........ 73/861.356 | JP | 57196619 | 2/1982 |
| 7,089,086 | B2 | 8/2006 | Schoonover ........ 700/275 | JP | 58-129316 | 8/1983 |
| 7,137,307 | B2 | 11/2006 | Huybrechts et al. ...... 73/861.12 | JP | 59-116811 | 7/1984 |
| 7,254,518 | B2 * | 8/2007 | Eryurek et al. ........ 702/183 | JP | 59-163520 | 9/1984 |
| 7,258,021 | B2 | 8/2007 | Broden ............... 73/756 | JP | 59176643 | 10/1984 |
| 7,258,024 | B2 | 8/2007 | Dimarco et al. ........ 73/861.22 | JP | 59-211196 | 11/1984 |
| 7,290,450 | B2 | 11/2007 | Brown et al. ........ 73/579 | JP | 59-211896 | 11/1984 |
| 7,321,846 | B1 | 1/2008 | Huisenga et al. ........ 702/183 | JP | 60-000507 | 1/1985 |
| 2002/0013629 | A1 | 1/2002 | Nixon et al. | JP | 60-76619 | 5/1985 |
| 2002/0032544 | A1 | 3/2002 | Reid et al. ........ 702/183 | JP | 60-131495 | 7/1985 |
| 2002/0077711 | A1 | 6/2002 | Nixon ............... 700/19 | JP | 60-174915 | 9/1985 |
| 2002/0078752 | A1 | 6/2002 | Braunling et al. ........ 73/627 | JP | 62-30915 | 2/1987 |
| 2002/0108436 | A1 | 8/2002 | Albuaijan ............... 73/168 | JP | 62-080535 | 4/1987 |
| 2002/0121910 | A1 | 9/2002 | Rome et al. ........ 324/718 | JP | 62-50901 | 9/1987 |
| 2002/0145515 | A1 | 10/2002 | Snowbarger et al. ........ 340/514 | JP | 63-169532 | 7/1988 |
| 2002/0145568 | A1 | 10/2002 | Winter ............... 343/701 | JP | 64-01914 | 1/1989 |
| 2002/0148644 | A1 | 10/2002 | Schultz et al. ........ 175/39 | JP | 64-72699 | 3/1989 |
| 2002/0194547 | A1 | 12/2002 | Christensen et al. ........ 714/43 | JP | 11-87430 | 7/1989 |
| 2003/0033040 | A1 | 2/2003 | Billings ............... 700/97 | JP | 2-05105 | 1/1990 |
| 2003/0045962 | A1 | 3/2003 | Eryurek et al. | JP | 3-229124 | 10/1991 |
| 2004/0025593 | A1 | 2/2004 | Hashimoto et al. ........ 73/643 | JP | 4-70906 | 3/1992 |
| 2004/0078167 | A1 | 4/2004 | Tan et al. ........ 702/181 | JP | 5-122768 | 5/1993 |
| 2004/0093174 | A1 | 5/2004 | Lander ............... 702/56 | JP | 6-95882 | 4/1994 |
| 2004/0128034 | A1 | 7/2004 | Lenker et al. ........ 700/282 | JP | 06242192 | 9/1994 |
| 2004/0249583 | A1 | 12/2004 | Eryurek et al. ........ 702/47 | JP | 06-248224 | 10/1994 |
| 2005/0072239 | A1 | 4/2005 | Longsdorf et al. ........ 73/649 | JP | 7-063586 | 3/1995 |
| 2006/0075009 | A1 | 4/2006 | Lenz et al. ........ 708/160 | JP | 07234988 | 9/1995 |
| 2006/0206288 | A1 | 9/2006 | Brahmajosyula et al. .... 702/183 | JP | 07294356 A2 | 11/1995 |
| 2006/0277000 | A1 * | 12/2006 | Wehrs ............... 702/183 | JP | 8-054923 | 2/1996 |
| | | | | JP | 8-102241 | 4/1996 |
| | | FOREIGN PATENT DOCUMENTS | | JP | 08-114638 | 5/1996 |
| | | | | JP | 8-136386 | 5/1996 |
| DE | 32 13 866 A1 | 10/1983 | | JP | HEI8/1996-136386 | 5/1996 |
| DE | 35 40 204 C1 | 9/1986 | | JP | 8-166309 | 6/1996 |
| DE | 40 08 560 A1 | 9/1990 | | JP | HEI8/1996-166309 | 6/1996 |
| DE | 43 43 747 | 6/1994 | | JP | 8-247076 | 9/1996 |
| DE | 44 33 593 A1 | 6/1995 | | JP | 8-313466 | 11/1996 |
| DE | 195 02 499 A1 | 8/1996 | | JP | 2712625 | 10/1997 |
| DE | 296 00 609 U1 | 3/1997 | | JP | 2712701 | 10/1997 |
| DE | 197 04 694 A1 | 8/1997 | | JP | 2753592 | 3/1998 |
| DE | 19930660 A1 | 7/1999 | | JP | 07225530 | 5/1998 |
| DE | 199 05 071 | 8/2000 | | JP | 10-232170 | 9/1998 |
| DE | 19905071 A1 | 8/2000 | | JP | 11-083575 | 3/1999 |
| DE | 299 17 651 U1 | 12/2000 | | JP | 3129121 | 11/2000 |
| DE | 19947129 | 4/2001 | | JP | 3139597 | 12/2000 |
| DE | 100 36 971 A1 | 2/2002 | | JP | 3147275 | 12/2000 |
| DE | 10223725 A1 | 4/2003 | | RU | 2001-19037/06 | 7/2000 |
| EP | 0 122 622 A1 | 10/1984 | | RU | 2190267 C2 | 9/2002 |
| EP | 0 413 814 A1 | 2/1991 | | WO | WO 94/25933 | 11/1994 |
| EP | 0 487 419 A2 | 5/1992 | | WO | WO 95/23361 | 8/1995 |
| EP | 0 512 794 A2 | 11/1992 | | WO | WO 96/11389 | 4/1996 |
| EP | 0 594 227 A1 | 4/1994 | | WO | WO 96/12993 | 5/1996 |
| EP | 0 624 847 A1 | 11/1994 | | WO | WO 96/39617 | 12/1996 |
| EP | 0 644 470 A2 | 3/1995 | | WO | WO 97/21157 | 6/1997 |
| EP | 0 697 586 A2 | 2/1996 | | WO | WO 97/25603 | 7/1997 |
| EP | 0 749 057 A1 | 12/1996 | | WO | WO 98/06024 | 2/1998 |
| EP | 0 825 506 A2 | 2/1998 | | WO | WO 98/13677 | 4/1998 |
| EP | 0 827 096 A2 | 9/1997 | | WO | WO 98/14855 | 4/1998 |
| EP | 0 838 768 A2 | 9/1997 | | WO | WO 98/20469 | 5/1998 |

| | | |
|---|---|---|
| WO | WO 98/39718 | 9/1998 |
| WO | WO 99/19782 | 4/1999 |
| WO | WO 00/41050 | 7/2000 |
| WO | WO 00/55700 | 9/2000 |
| WO | WO 00/70531 | 11/2000 |
| WO | WO 01/01213 A1 | 1/2001 |
| WO | WO 01/19440 A1 | 3/2001 |
| WO | WO 01/59346 | 8/2001 |
| WO | WO 01/77766 | 10/2001 |
| WO | WO 01/90704 A2 | 11/2001 |
| WO | WO 02/27418 | 4/2002 |
| WO | WO 03/048713 | 6/2003 |
| WO | WO 03/081002 A1 | 10/2003 |

OTHER PUBLICATIONS

"Invitation to Pay Additional Fees and Annex to Form PCT/ISA/206".
U.S. Appl. No. 10/893,144, filed Jul. 2004, Brown et al.
U.S. Appl. No. 09/257,896, filed Feb. 25, 1999, Eryurek et al.
U.S. Appl. No. 09/409,098, filed Sep. 30, 1999, Eryurek et al.
U.S. Appl. No. 09/799,824, filed Mar. 5, 2001, Rome et al.
U.S. Appl. No. 09/855,179, filed May 14, 2001, Eryurek et al.
U.S. Appl. No. 09/852,102, filed May 9, 2001, Eryurek et al.
U.S. Appl. No. 09/972,078, filed Oct. 5, 2001, Eryurek et al.
U.S. Appl. No. 10/635,944, filed Aug. 7, 2003, Huisenga et al.
"A TCP/IP Tutorial" by, Socolofsky et al., Spider Systems Limited, Jan. 1991 pp. 1-23.
"Approval Standards For Explosionproof Electrical Equipment General Requirements", Factory Mutual Research, Cl. No. 3615, Mar. 1989, pp. 1-34.
"Approval Standard Intrinsically Safe Apparatus and Associated Apparatus For Use In Class I, II, and III, Division 1 Hazardous (Classified) Locations", Factory Mutual Research, Cl. No. 3610, Oct. 1988, pp. 1-70.
"Automation On-line" by, Phillips et al., Plant Services, Jul. 1997, pp. 41-45.
"Climb to New Heights by Controlling your PLCs Over the Internet" by, Phillips et al., Intech, Aug. 1998, pp. 50-51.
"CompProcessor For Piezoresistive Sensors" MCA Technologies Inc. (MCA7707), pp. 1-8.
"Ethernet emerges as viable, inexpensive fieldbus", Paul G. Schreier, Personal Engineering, Dec. 1997, p. 23-29.
"Ethernet Rules Closed-loop System" by Eidson et al., Intech, Jun. 1998, pp. 39-42.
"Fieldbus Standard for Use in Industrial Control Systems Part 2: Physical Layer Specification and Service Definition", ISA-S50.02-1992, pp. 1-93.
"Fieldbus Standard for Use in Industrial Control Systems Part 3: Data Link Service Definition", ISA-S50.02-1997, Part 3, Aug. 1997, pp. 1-159.
Fieldbus Standard For Use in Industrial Control Systems Part 4: Data Link Protocol Specification, ISA-S50.02-1997, Part 4, Aug. 1997, pp. 1-148.
"Fieldbus Support For Process Analysis" by, Blevins et al., Fisher-Rosemount Systems, Inc., 1995, pp. 121-128.
"Fieldbus Technical Overview Understanding Foundation™ fieldbus technology", Fisher-Rosemount, 1998, pp. 1-23.
"Hypertext Transfer Protocol—HTTP/1.0" by, Berners-Lee et al., MIT/LCS, May 1996, pp. 1-54.
"Infranets, Intranets, and the Internet" by, Pradip Madan, Echelong Corp, Sensors, Mar. 1997, pp. 46-50.
"Internet Technology Adoption into Automation" by, Fondl et al., Automation Business, pp. 1-5.
"Internet Protocol Darpa Internet Program Protocol Specification" by, Information Sciences Institute, University of Southern California, RFC 791, Sep. 1981, pp. 1-43.
"Introduction to Emit", emWare, Inc., 1997, pp. 1-22.
"Introduction to the Internet Protocols" by, Charles L. Hedrick, Computer Science Facilities Group, Rutgers University, Oct. 3, 1988, pp. 1-97.
"Is There A Future For Ethernet in Industrial Control?", Miclot et al., Plant Engineering, Oct. 1988, pp. 44-46, 48, 50.

LFM/SIMA Internet Remote Diagnostics Research Project Summary Report, Stanford University, Jan. 23, 1997, pp. 1-6.
"Managing Devices with the Web" by, Howard et al., Byte, Sep. 1997, pp. 45-64.
"Modular Microkernel Links GUI And Browser For Embedded Web Devices" by, Tom Williams, pp. 1-2.
"PC Software Gets Its Edge From Windows, Components, and the Internet", Wayne Labs, I&CS, Mar. 1997, pp. 23-32.
Proceedings Sensor Expo, Aneheim, California, Produced by Expocon Managemnet Associates, Inc., Apr. 1996, pp. 9-12.
Proceedings Sensor Expo, Boston, Massachuttes, Produced by Expocon Management Associates, Inc., May 1997, pp. 1-416.
"Smart Sensor Network of the Future" by, Jay Warrior, Sensors, Mar. 1997, pp. 40-45.
"The Embedded Web Site" by, John R. Hines, IEEE Spectrum, Sep. 1996, p. 23.
"Transmission Control Protocol: Darpa Internet Program Protocol Specification" Information Sciences Institute, Sep. 1981, pp. 1-69.
"On-Line Statistical Process Control for a Glass Tank Ingredient Scale," by R.A. Weisman, *IFAC real Time Programming*, 1985, pp. 29-38.
"The Performance of Control Charts for Monitoring Process Variation," by C. Lowry et al., *Commun. Statis.—Simula.*, 1995, pp. 409-437.
"A Knowledge-Based Approach for Detection and Diagnosis of Out-Of-Control Events in Manufacturing Processes," by P. Love et al., *IEEE*, 1989, pp. 736-741.
"Advanced Engine Diagnostics Using Universal Process Modeling", by P. O'Sullivan, *Presented at the 1996 SAE Conference on Future Transportation Technology*, pp. 1-9.
Parallel, Fault-Tolerant Control and Diagnostics System for Feedwater Regulation in PWRS, by E. Eryurek et al., *Proceedings of the American Power Conference*.
"Programmable Hardware Architectures for Sensor Validation", by M.P. Henry et al., *Control Eng. Practice*, vol. 4, No. 10., pp. 1339-1354, (1996).
"Sensor Validation for Power Plants Using Adaptive Backpropagation Neural Network," *IEEE Transactions on Nuclear Science*, vol. 37, No. 2, by E. Eryurek et al. Apr. 1990, pp. 1040-1047.
"Signal Processing, Data Handling and Communications: The Case for Measurement Validation", by M.P. Henry, *Department of Engineering Science*, Oxford University.
"Smart Temperature Measurement in the '90s", by T. Kerlin et al., *C&I*, (1990).
"Software-Based Fault-Tolerant Control Design for Improved Power Plant Operation," *IEEE/IFAC Joint Symposium on Computer-Aided Control System Design*, Mar. 7-9, 1994 pp. 585-590.
A Standard Interface for Self-Validating Sensors, by M.P. Henry et al., *Report No. QUEL 1884/91*, (1991).
"Taking Full Advantage of Smart Transmitter Technology Now," by G. Orrison, *Control Engineering*, vol. 42, No. 1, Jan. 1995.
"Using Artificial Neural Networks to Identify Nuclear Power Plant States," by Israel E. Alguindigue et al., pp. 1-4.
"Application of Neural Computing Paradigms for Signal Validation," by B.R. Upadhyaya et al., *Department of Nuclear Engineering*, pp. 1-18.
"Application of Neural Networks for Sensor Validation and Plant Monitoring," by B. Upadhyaya et al., *Nuclear Technology*, vol. 97, No. 2, Feb. 1992 pp. 170-176.
"Automated Generation of Nonlinear System Characterization for Sensor Failure Detection," by B.R. Upadhyaya et al., *ISA*, 1989 pp. 269-274.
"In Situ Calibration of Nuclear Plant Platinum Resistance Thermometers Using Johnson Noise Methods," *EPRI*, Jun. 1983.
"Johnson Noise Thermometer for High Radiation and High-Temperature Environments," by L. Oakes et al., *Fifth Symposium on Space Nuclear Power Systems*, Jan. 1988, pp. 2-23.
"Development of a Resistance Thermometer For Use Up to 1600° C", by M.J. de Groot et al., *CAL LAB*, Jul./Aug. 1996, pp. 38-41.
"Survey, Applications, And Prospects of Johnson Noise Thermometry," by T. Blalock et al., *Electrical Engineering Department*, 1981 pp. 2-11.

"Noise Thermometry for Industrial and metrological Applications at KFA Julich," by H. Brixy et al., *7th International Symposium on Temperature*, 1992.

"Johnson Noise Power Thermometer and its Application in Process Temperature Measurement," by T.V. Blalock et al., *American Institute of Physics* 1982, pp. 1249-1259.

"Field-based Architecture is Based on Open Systems, Improves Plant Performance", by P. Cleaveland, *I&CS*, Aug. 1996, pp. 73-74.

"Tuned-Circuit Dual-Mode Johnson Noise Thermometers," by R.L. Shepard et al., Apr. 1992.

"Tuned-Circuit Johnson Noise Thermometry," by Michael Roberts et al., *7th Symposium on Space Nuclear Power Systems*, Jan. 1990.

"Smart Field Devices Provide New Process Data, Increase System Flexibility," by Mark Boland, *I&CS*, Nov. 1994, pp. 45-51.

"Wavelet Analysis of Vibration, Part I: Theory[1]," by D.E. Newland, *Journal of Vibration and Acoustics*, vol. 116, Oct. 1994, pp. 409-416.

"Wavelet Analysis of Vibration, Part 2: Wavelet Maps," by D.E. Newland, *Journal of Vibration and Acoustics*, vol. 116, Oct. 1994, pp. 417-425.

"Development of a Long-Life, High-Reliability Remotely Operated Johnson Noise Thermometer," by R.L. Shepard et al., *ISA*, 1991, pp. 77-84.

"Application of Johnson Noise Thermometry to Space Nuclear Reactors," by M.J. Roberts et al., *Presented at the 6th Symposium on Space Nuclear Power Systems*, Jan. 9-12, 1989.

"A Decade of Progress in High Temperature Johnson Noise Thermometry," by T.V. Blalock et al., *American Institute of Physics*, 1982 pp. 1219-1223.

"Sensor and Device Diagnostics for Predictive and Proactive Maintenance", by B. Boynton, *A Paper Presented at the Electric Power Research Institute—Fossil Plant Maintenance Conference* in Baltimore, Maryland, Jul. 29-Aug. 1, 1996, pp. 50-1-50-6.

"Detection of Hot Spots in Thin Metal Films Using an Ultra Sensitive Dual Channel Noise Measurement System," by G.H. Massiha et al., *Energy and Information Technologies in the Southeast*, vol. 3 of 3, Apr. 1989, pp. 1310-1314.

"Detecting Blockage in Process Connections of Differential Pressure Transmitters", by E. Taya et al., *SICE*, 1995, pp. 1605-1608.

"Development and Application of Neural Network Algorithms For Process Diagnostics," by B.R. Upadhyaya et al., *Proceedings of the 29th Conference on Decision and Control*, 1990, pp. 3277-3282.

"A Fault-Tolerant Interface for Self-Validating Sensors", by M.P. Henry, *Colloquium*, pp. 3/1-3/2 (Nov. 1990).

"Fuzzy Logic and Artificial Neural Networks for Nuclear Power Plant Applications," by R.C. Berkan et al., *Proceedings of the American Power Conference*.

"Fuzzy Logic and Neural Network Applications to Fault Diagnosis", by P. Frank et al., *International Journal of Approximate Reasoning*, (1997), pp. 68-88.

"Keynote Paper: Hardware Compilation-A New Technique for Rapid Prototyping of Digital Systems-Applied to Sensor Validation", by M.P. Henry, *Control Eng. Practice*, vol. 3, No. 7., pp. 907-924, (1995).

"The Implications of Digital Communications on Sensor Validation", by M. Henry et al., *Report No. QUEL 1912/92*, (1992).

"In-Situ Response Time Testing of Thermocouples", *ISA*, by H.M. Hashemian et al., Paper No. 89-0056, pp. 587-593, (1989).

"An Integrated Architecture For Signal Validation in Power Plants," by B.R. Upadhyaya et al., *Third IEEE International Symposium on Intelligent Control*, Aug. 24-26, 1988, pp. 1-6.

"Integration of Multiple Signal Validation Modules for Sensor Monitoring," by B. Upadhyaya et al., *Department of Nuclear Engineering*, Jul. 8, 1990, pp. 1-6.

"Intelligent Behaviour for Self-Validating Sensors", by M.P. Henry, *Advances In Measurement*, pp. 1-7, (May 1990).

"Measurement of the Temperature Fluctuation in a Resistor Generating 1/F Fluctuation," by S. Hashiguchi, *Japanese Journal of Applied Physics*, vol. 22, No. 5, Part 2, May 1983, pp. L284-L286.

"Check of Semiconductor Thermal Resistance Elements by the Method of Noise Thermometry," by A. B. Kisilevskii et al., *Measurement Techniques*, vol. 25, No. 3, Mar. 1982, New York, USA, pp. 244-246.

"Neural Networks for Sensor Validation and Plant Monitoring," by B. Upadhyaya, *International Fast Reactor Safety Meeting*, Aug. 12-16, 1990, pp. 2-10.

"Neural Networks for Sensor Validation and Plantwide Monitoring," by E. Eryurek, 1992.

"A New Method of Johnson Noise Thermometry", by C.J. Borkowski et al., *Rev. Sci. Instrum.*, vol. 45, No. 2, (Feb. 1974) pp. 151-162.

"Thermocouple Continuity Checker," IBM Technical Disclosure Bulletin, vol. 20, No. 5, pp. 1954 (Oct. 1977).

"A Self-Validating Thermocouple," Janice C-Y et al., IEEE Transactions on Control Systems Technology, vol. 5, No. 2, pp. 239-253 (Mar. 1997).

*Instrument Engineers' Handbook*, Chapter IV entitled "Temperature Measurements," by T.J. Claggett, pp. 266-333 (1982).

"emWare's Releases EMIT 3.0, Allowing Manufacturers to Internet and Network Enable Devices Royalty Fees," 3 pages, PR Newswire (Nov. 4, 1998).

Warrior, J., "The IEEE P1451.1 Object Model Network Independent Interfaces for Sensors and Actuators," pp. 1-14, Rosemount Inc. (1997).

Warrior, J., "The Collision Between the Web and Plant Floor Automation," 6[Th]. WWW Conference Workshop on Embedded Web Technology, Santa Clara, CA (Apr. 7, 1997).

Microsoft Press Computer Dictionary, 3rd Edition, p. 124.

"Internal Statistical Quality Control for Quality Monitoring Instruments", by P. Girling et al., *ISA*, 15 pgs., 1999.

Web Pages from www.triant.com (3 pgs.).

"Statistical Process Control (Practice Guide Series Book)", *Instrument Society of America*, 1995, pp. 1-58 and 169-204.

"Time-Frequency Analysis of Transient Pressure Signals for a Mechanical Heart Valve Cavitation Study," *ASAIO Journal*, by Alex A. Yu et al., vol. 44, No. 5, pp. M475-M479, (Sep.-Oct. 1998).

"Transient Pressure Signals in Mechanical Heart Valve Caviation," by Z.J. Wu et al., pp. M555-M561 (undated).

"Caviation in Pumps, Pipes and Valves," *Process Engineering*, by Dr. Ronald Young, pp. 47 and 49 (Jan. 1990).

"Quantification of Heart Valve Cavitation Based on High Fidelity Pressure Measurements," *Advances in Bioengineering 1994*, by Laura A. Garrison et al., BED-vol. 28, pp. 297-298 (Nov. 6-11, 1994).

"Monitoring and Diagnosis of Cavitation in Pumps and Valves Using the Wigner Distribution," *Hydroaccoustic Facilities, Instrumentation, and Experimental Techniques*, NCA-vol. 10, pp. 31-36 (1991).

"Developing Predictive Models for Cavitation Erosion," *Codes and Standards in A Global Environment*, PVP-vol. 259, pp. 189-192 (1993).

"Self-Diagnosing Intelligent Motors: A Key Enabler for Next Generation Manufacturing System," by Fred M. Discenzo et al., pp. 3/1-3/4 (1999).

"A Microcomputer-Based Instrument for Applications in Platinum Resistance Thermomety," by H. Rosemary Taylor and Hector A. Navarro, Journal of Physics E. Scientific Instrument, vol. 16, No. 11, pp. 1100-1104 (1983).

"Experience in Using Estelle for the Specification and Verification of a Fieldbus Protocol: FIP," by Barretto et al., Computer Networking, pp. 295-304 (1990).

"Computer Simulation of Hl Field Bus Transmission," by Utsumi et al., Advances in Instrumentation and Control, vol. 46, Part 2, pp. 1815-1827 (1991).

"Progress in Fieldbus Developments for Measuring and Control Application," by A. Schwaier, Sensor and Acuators, pp. 115-119 (1991).

"Ein Emulationssystem zur Leistungsanalyse von Feldbussystemen, Teil 1," by R. Hoyer, pp. 335-336 (1991).

"Simulatore Integrato: Controllo su bus di campo," by Barabino et al., Automazione e Strumentazione, pp. 85-91 (Oct. 1993).

"Ein Modulares, verteiltes Diagnose-Expertensystem für die Fehlerdiagnose in lokalen Netzen," by Jürgen M. Schröder, pp. 557-565 (1990).

"Fault Diagnosis of Fieldbus Systems," by Jürgen Quade, pp. 577-581 (Oct. 1992).

"Ziele und Anwendungen von Feldbussystemen," by T. Pfeifer et al., pp. 549-557 (Oct. 1987).

"PROFIBUS Infrastructure Measures," by Tilo Pfeifer et al., pp. 416-419 (Aug. 1991).
"Simulation the Time Behaviour of Fieldbus Systems," by O. Schnelle, pp. 440-442 (1991).
"Modélisation et simulation d'un bus de terrain: FIP," by Song et al, pp. 5-9 (undated).
"Field Bus Networks for Automation Systems Containing Intelligent Functional Unites," by W. Kriesel et al., pp. 486-489 (1987).
"Field Buses for Process Interconnection with Digital Control Systems," Tecnología, pp. 141-147 (1990).
"Decentralised Systems with Real-Time Field Bus," Netzwerke, Jg. Nr. 3 v. 14.3, 4 pages (1990).
"Process Measurement and Analysis," by Liptak et al., Instrument Engineers' Handbook, Third Edition, pp. 528-530, (1995).
"Improving Dynamic Performance of Temperature Sensors With Fuzzy Control Techniques," by Wang Lei et al., pp. 872-873 (1992).
"Microsoft Press Computer Dictionary" 2nd Edition, 1994, Microsoft Press. p. 156.
International Search Report from Application No. PCT/US01/40791 with international filing date of May 22, 2001.
International Search Report from Application No. PCT/US01/40782 with international filing date of May 22, 2001.
International Search Report from Application No. PCT/02/14560 with international filing date of May 8, 2002.
International Search Report from Application No. PCT/US02/14934 with international filing date of May 8, 2002.
"On-Line Tool Condition Monitoring System With Wavelet Fuzzy Neural Network," by Li Xiaoli et al., pp. 271-276 (1997).
"Optimal Design of the Coils of An Electromagnetic Flow Meter," by Michalski, A. et al., IEEE Transactions on Magnetics, vol. 34, Issue 5, Part 1, pp. 2563-2566 (1998).
"Magnetic Fluid Flow Meter for Gases," Popa, N.C., IEEE Transactions on Magnetics, vol. 30, Issue 2, Part 1-2, pp. 936-938 (1993).
"New Approach to A Main Error Estimation for Primary Transducer of Electromagnetic Flow Meter," by Michalski, A., IEEE Instrumentation and Measurement Technology Conference Proceedings, vol. 2, pp. 1093-1097 (1998).
"Additional Information From Flowmeters Via Signal Analysis," by Amadi-Echendu, J.E. et al., IEEE Instrumentation and Measurement Technology Conference Record, vol. 7, pp. 187-193 (1990).
International Search Report from Application No. PCT/US02/06606 with international filing date of Mar. 5, 2002.
International Search Report from Application No. PCT/US02/30465 with international filing date of Sep. 25, 2002.
"What is a weighted moving average?", *Dau Stat Refresher*, http://cne.gmu.edu/modules/dau/stat/mvavgs/wma__bdy.html. (1995).
U.S. Appl. No. 10/675,014, filed Sep. 2003, Longsdorf et al.
U.S. Appl. No. 10/744,809, filed Dec. 2003, Brown et al.
"Statistics Glossary: Time Series Data", by Easton et al., http://www.stats.gla.ac.uk/steps/glossary/time_series.html, Sep. 1997.
"The Indicators Story", Sustainable Seattle, pp. 55-59, 1998.
"Detecting Regimes in Temperature Time Series", by Clemins et al., *Artificial Neural Networks in Engineering, Proceedings*, pp. 727-732, 2001.
"Re: Digital Filter-Moving Average", The Math Forumn, http://mathforum.org/discuss/sci.math/a/t/177212, Sep. 28, 1998.
"Invitation to Pay Additional Fees" PCT/US2004/031678.
"Notification of Transmittal of the International Search Report and the Written Opinion" PCT/US2004/022736.
"Notification of Transmittal of the International Search Report" PCT/US00/14798.
"Gas Pipeline Monitoring by Acoustic Method", by H. Koyama et al., *Transactions of the Society of Instrument and Control Engineers*, vol. 29, No. 3, pp. 295-301, 1993.
"Experience with the Acoustic Ranger-A sound Method for Tube Inspection", by E.S. Morgan, *Materials Evaluation*, Columbus, OH, vol. 39, pp. 926-930, Sep. 1981.
"On-Line Detection of Blockages in Pressure Sensing Systems", by D.W. Mitchell et al., *ASME/JSME Nuclear Engineering Conference*, vol. 2, pp. 775-781, Mar. 1993.
"Detecting Blockage in Process Connections of Differential Pressure Transmitters", by E. Taya et al., *SICE 95-Proceedings of the 34th SICE Annual Conference*, pp. 1605-1608, Jul. 1995.
"Invitation to Pay Additional Fees-Annex to Form PCT/ISA/206 Communication Relating to the Results of the Partial International Search", PCT/US2004/041490.
"Notification of Transmittal of The International Search Report and the Written Opinion of the International Searching Authority or the Declaration", PCT/US2004/041490.
International Search Report and Written Opinion for corresponding Application No. PCT/US2005/020010, filed Jun. 7, 2005.
Chinese Office Action from corresponding Chinese Patent Application No. 200480036420X.
"Office Action" from related U.S. Appl. No. 11/439,095.
"Notification of Transmittal of International Search Report and the Written Opinion", PCT/US2006/037535.
Notification Concerning Transmittal of Copy of International Preliminary Report of Patentability (Chapter I of the Patent Cooperation Treaty), PCT/US2004/041490.

* cited by examiner

DIAGNOSTICS OF IMPULSE PIPING IN AN INDUSTRIAL PROCESS

BACKGROUND OF THE INVENTION

The present invention relates to process devices. More particularly, the present invention relates to process devices which coupled to process fluid through process piping.

Various types of process devices are used to measure process variables and couple to process fluid through process piping. For example, fluid flow meters are used in industrial process control environments to measure fluid flow and provide outputs related to flow indicators and process controllers. Inferential flow meters measure fluid flow in a pipe by measuring a pressure drop near a discontinuity within the pipe. The discontinuity (primary element) can be an orifice, a nozzle, a venturi, a pitot tube, a vortex shedding bar, a target or even a simple bend in the pipe. Flow around the discontinuity causes both a pressure drop and increased turbulence. The pressure drop is sensed by a pressure transmitter (secondary element) placed outside the pipe and connected by impulse lines or impulse passageways to the fluid in the pipe. These connections are also referred to as impulse piping. Reliability depends on maintaining a correct calibration. Impulse lines can become plugged over time, which also adversely affects calibration.

Disassembly and inspection of the impulse lines is one method used to identify and correct plugging of lines. Another known method for detecting plugging is to periodically add a "check pulse" to the measurement signal from a pressure transmitter. This check pulse causes a control system connected to the transmitter to disturb the flow. If the pressure transmitter fails to accurately sense the flow disturbance, an alarm signal is generated indicating line plugging. Another known method for detecting plugging is sensing of both static and differential pressures. If there is inadequate correlation between oscillations in the static and differential pressures, then an alarm signal is generated indicating line plugging. Still another known method for detecting line plugging is to sense static pressures and pass them through high pass and low pass filters. Noise signals obtained from the filters are compared to a threshold, and if variance in the noise is less than the threshold, an alarm signal can be triggered which indicates that the line is blocked.

These known methods rely on providing static pressure sensors, disassembly of the flow meter or use of an external control system for diagnostics. The methods increase complexity and reduce reliability. There is thus a need for improved diagnostic technology that can provide more predictive, less reactive maintenance to reduce cost or improve reliability.

SUMMARY

An apparatus and method for diagnosing operation of impulse piping lines in an industrial process is provided. A vibration source transmits a vibration signal through the piping to a receiver configured to receive the vibration signal. Operation of the piping is diagnosed based upon the received vibration signal.

DETAILED DESCRIPTION

Figure 1:
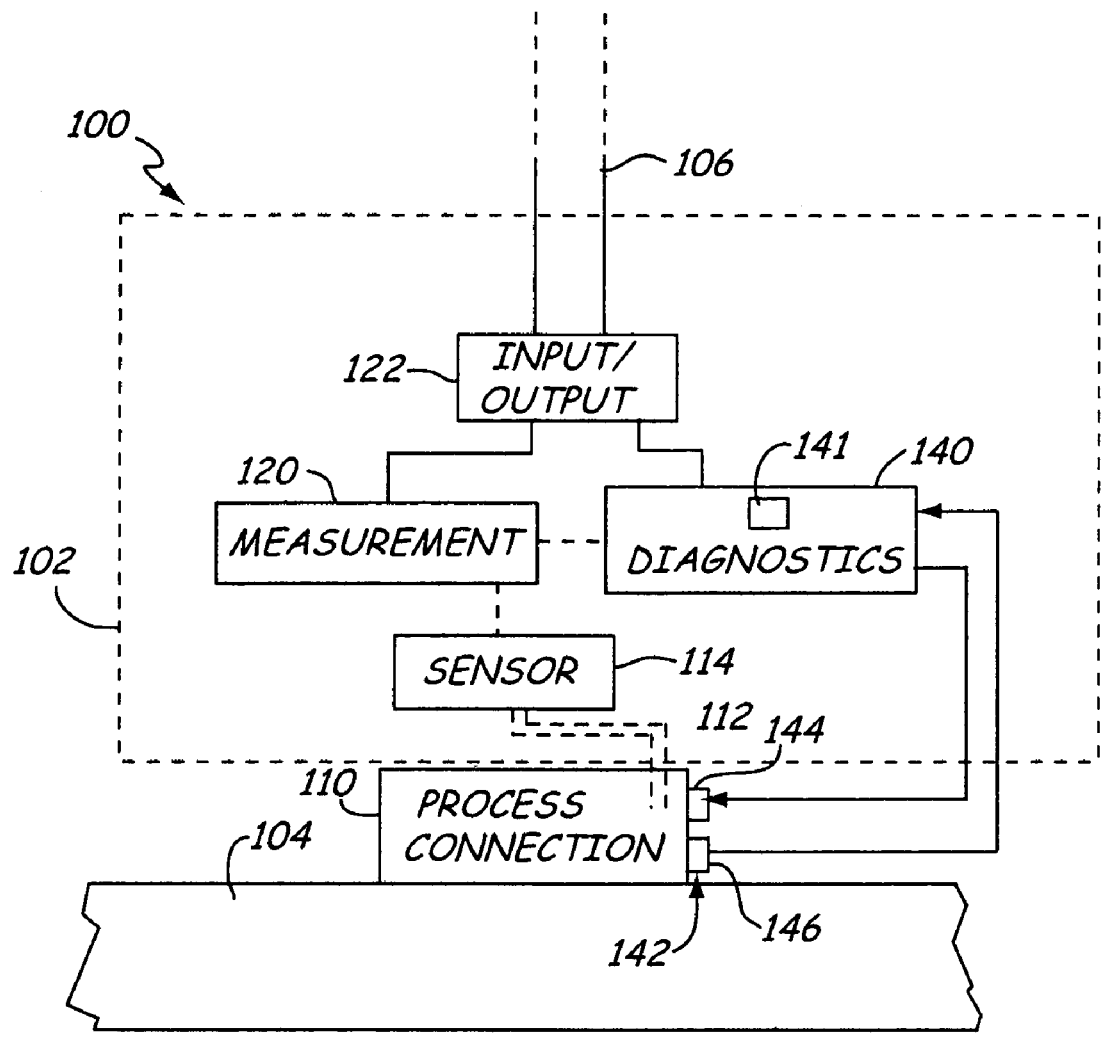
FIG. 1 is a simplified block diagram showing a process device that includes process impulse piping diagnostics of the invention.

FIG. 1 is a partial view of a process control or monitoring system 100 which includes a process transmitter 102 coupled to process pipe 104. Process pipe 104 can be any type of vessel which carries process fluid including, for example, a storage container. Process pipe 104 carries a process fluid and transmitter 102 is configured to measure a process variable of the process fluid, such as pressure, and provide an output. One example output is a two-wire process control loop 106 which operates in accordance with standardized communication protocols such as the HART® Protocol, Fieldbus, Profibus, or others.

Transmitter 102 couples to the process fluid through a process connection 110. The process connection provides impulse piping 112 which extends between the process fluid and a sensor, for example a pressure sensor 114. The impulse piping 112 can be a direct fluid connection which carries process fluid and, in some embodiments, can include an isolation diaphragm if desired to isolate a fill fluid which couples to the sensor 114 from the process fluid.

During operation, it is possible for impulse piping 112 to become clogged. The clogging can be either partial or complete. As discussed in the Background section, various techniques have been used to diagnose and identify such plugging of impulse piping 112. Partial plugging can be particularly difficult to identify because the impulse piping is not completely blocked, and the sensor 114 continues to report data which may be inaccurate.

The present invention provides a technique for identifying clogging or plugging of process impulse piping 112. In the embodiment illustrated in FIG. 1, process transmitter 102 includes measurement circuitry 120 coupled to sensor 114. Input/output circuitry 122 couples to process control loop 106 and provides an output for measurement circuitry 120 which is related to the output of sensor 114. For example, this output can be related to the pressure of the process fluid, the flow rate of the process fluid, the level of the process fluid or other process variables.

In accordance with one embodiment of the present invention, transmitter 100 includes diagnostic circuitry 140 having memory 141. Diagnostic circuitry 140 couples to a transducer 142. Transducer 142 is physically connected to process impulse piping 112, for example by coupling to process connection 110 or by other connections. The transducer 142 can be a single transducer or can be two separate transducers formed by signal source 144 and signal receiver 146. In some embodiments, transducer 146 is a single element which provides both a send and receive function. The sending and receiving can be continuously operative or can be multiplexed.

In accordance with one embodiment, signal source 144 is a vibration signal source which sends a vibration signal into impulse piping line 112. The spectral content of the vibrations can be selected as desired. For example, the spectral content can comprise substantially random noise at relatively constant amplitude having frequencies which are lower than a selected upper limit. For reflected signal based diagnostics, a higher frequency acoustic frequency range is advantageous. Higher frequencies are more directional, and will reflect back more readily from build up sites along a partially plugged line. Since plugging sites create a low pass filter, a low frequency signal may not reflect from a plugging site, but rather may be transmitted, depending on the low pass filter characteristics. Also, short burst acoustic signals are more easily generated using higher frequencies, which can allow determining the position of the interface which provides the reflection. This is especially important in wet and dry leg level height diagnostics. Frequencies up to 40 KHz are useful for this type of burst mode signal. The burst mode signal also allows listening to the process noise spectrum for abnormal noise patterns between bursts. It is important that the burst noise frequency, or frequencies, not be masked by the process noise. In an optimal embodiment, the exact frequency, or frequencies of the transmitted interrogation signal would be changed for maximum signal to noise ratio versus the measured background noise spectrum.

The diagnostics of the present invention does not rely on ambient noise and instead utilizes source 144 to generate vibration noise. Receiver 146 is configured to receive vibration noise from impulse line 112 and provide a signal to diagnostic circuitry 140. Because the noise source 144 provides random noise with either a constant profile, or a profile adjusted as desired, diagnostic circuitry 140 can discriminate variations in the received signal and identify whether the source of the variations is due to changes in the plugging of impulse line 112 or is due to changes in the vibration signal applied by source 144. The transducer 146 can be coupled to a process manifold as a separate component or can be contained within the body of transmitter 102. Any appropriate transmitter and receiver configuration can be used. One type of transducing element is a piezoelectric element which is preferably adapted for high temperature installations. However, any technology can be used including electromechanical, etc. In order to improve efficiency, the piezoelectric element can be efficiently coupled to a manifold in the desired direction of acoustic energy travel, and decoupled in other directions. This configuration increases the applied noise signal and sensitivity in a desired direction.

Figure 2:
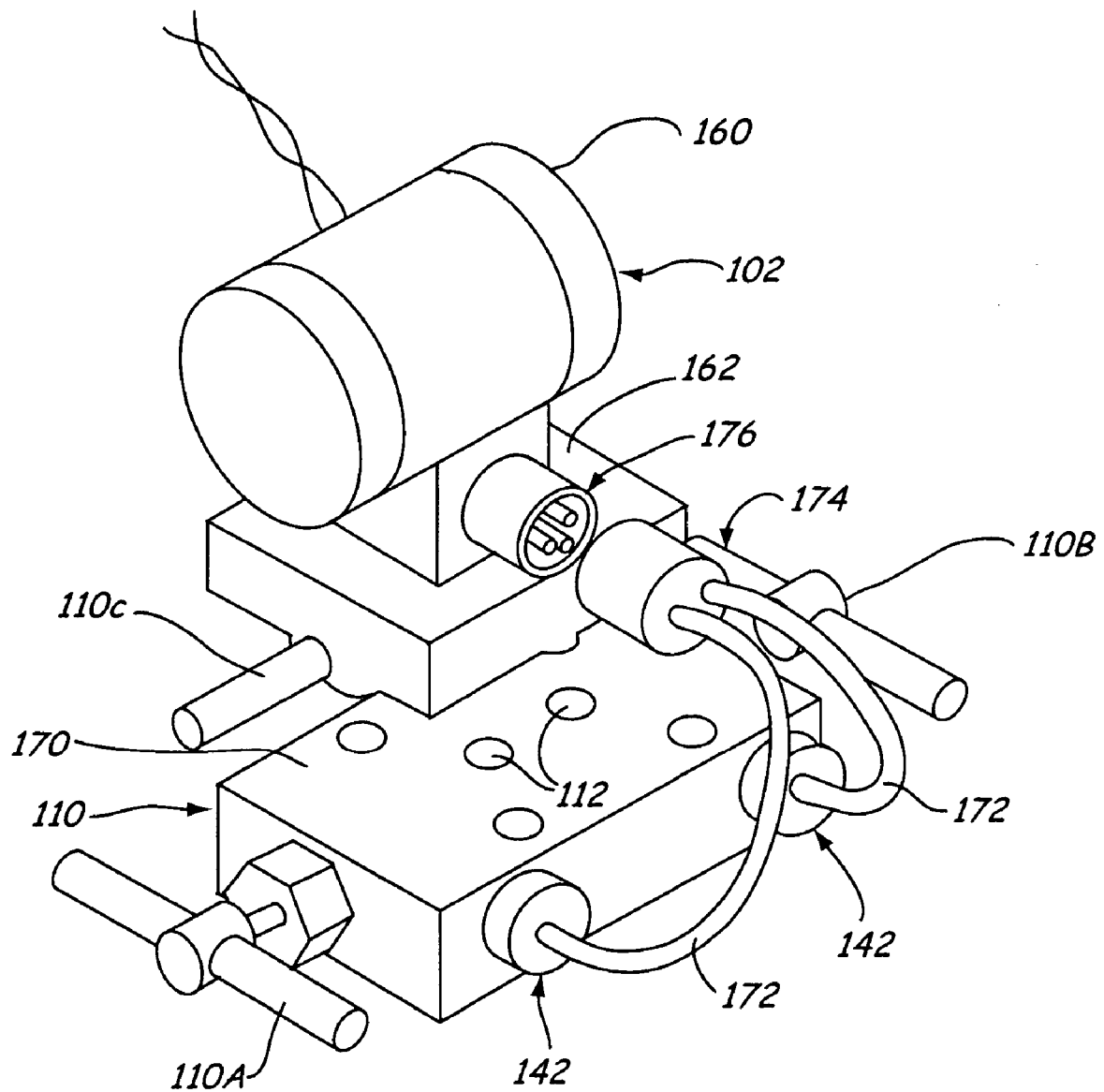
FIG. 2 is an exploded perspective view of a transmitter and a process coupling.

According to one embodiment, FIG. 2 is a perspective exploded view of process transmitter 102 adjacent process coupling 110. However, coupling 110 can be any type of coupling or flange configuration. In FIG. 2, process coupling 110 is illustrated as a three valve manifold flange which is used to connect a differential pressure transmitter to process pipe 104. Flange 110 includes blocking valves 110A and 110B, and equalizing valve 110C. Differential pressure measurements can be, for example, used to measure flow rate or product level. Process transmitter 102 includes a sensor module 162 connected to measurement module 160. Sensor module 162 includes a differential pressure sensor which couples to the process fluid through a series of process impulse piping lines. Typically, isolation diaphragms (not shown) are contained in the face of transmitter 102 which mounts to the face 170 of process coupling 110. The portion of the impulse piping 112 which extends through the process coupling 110 can be seen in FIG. 2.

Pursuant to one embodiment, transducers 142 couple to the side of process coupling 110 and connect to diagnostic circuitry 140 (shown in FIG. 1) of transmitter 102 through wiring 172, plug 174 and receptacle 176. Preferably, the plug 174 and receptacle 176 are configured to meet intrinsic safety requirements and provide hermetic seal against the environment. In FIG. 2, two transducers 142 are shown and are used for diagnosing plugging of the two impulse connections 112 through process coupling 110. It is appreciated that for other applications such as measuring absolute or gauge pressure, only one transducer would be needed for the one impulse line.

Figure 3A:
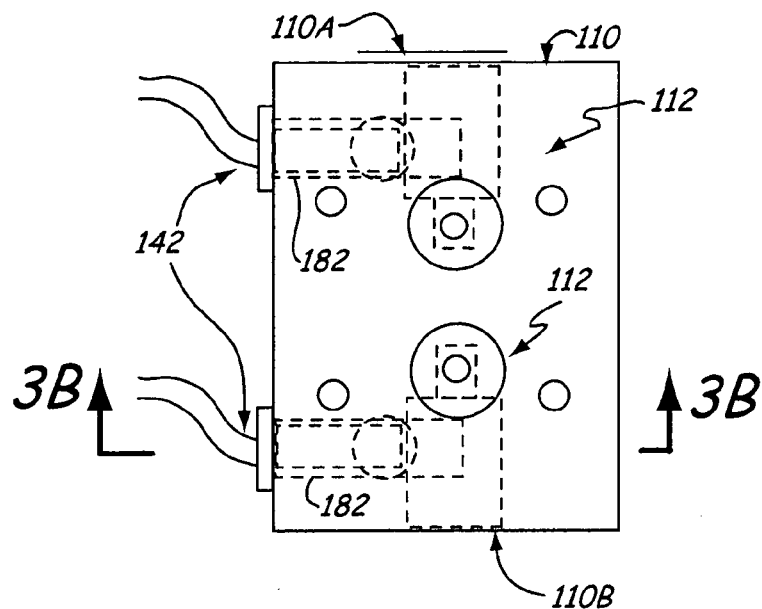
FIG. 3A is a top plan view.

FIG. 3A is a top plan view of process coupling 110 with transducers 142 mounted on its side. Process coupling 110 includes blocking valves 110A and 110B which are configured to block the impulse piping 112. Transducers 142 extend through holes 182 and into impulse piping 112.

Figure 3B:
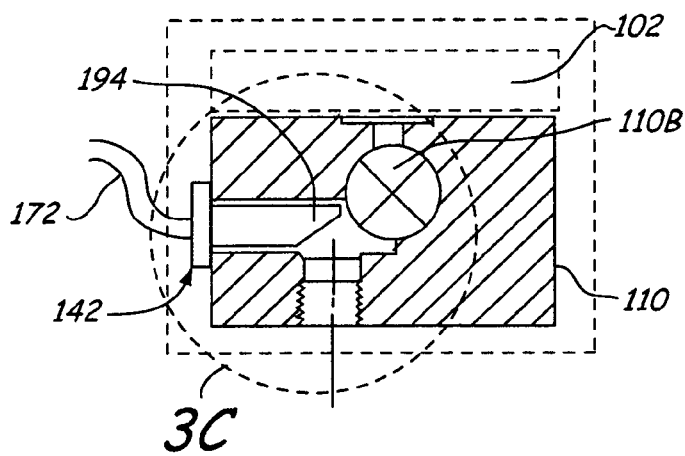
FIG. 3B is a side cross-sectional view and FIG. 3C is a cutaway cross-sectional view of the process coupling shown in FIG. 2.
Figure 3C:
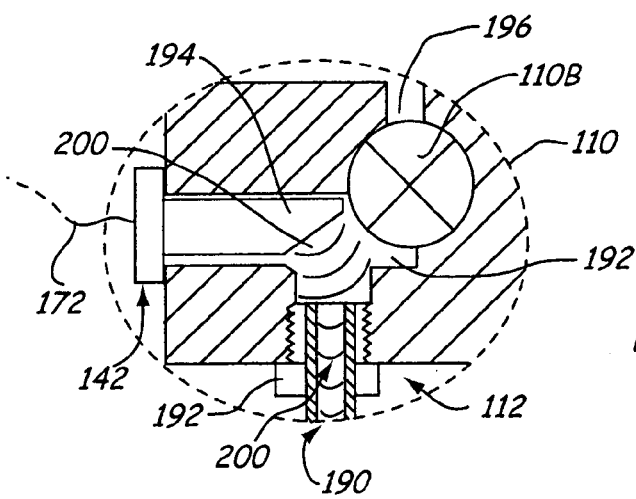

FIG. 3B is a side cross-sectional view of the process coupling 110 shown in FIG. 3A and FIG. 3C is an enlarged cutaway view of the cross-section shown in FIG. 3B. As illustrated in FIG. 3C, impulse piping 112 is formed of a number of components. Impulse piping 112 includes process connection piping 190 which couples to process pipe 104 shown in FIG. 1. Piping 190 connects to process coupling 110 through fitting 192. A main cavity 194 in body 110 is configured to receive piping 190, a tip portion 194 of transducer 142 and valve 110B. Valve 110B is configured to seal cavity 192 from transmitter connection 196 as desired.

As illustrated in FIG. 3C, a vibration signal 200 is transmitted and received by transducer 142 through the process impulse piping 112. In the embodiment of FIG. 3C, the tip 194 of transducer 142 is beveled and configured to direct the vibration signal 200 in a direction away from the transmitter 102. While the transducer 142 is illustrated as coupled to transmitter 102, other configurations can be used including a separate connection to the transducers 142 which does not require power from the transmitter 102.

During operation, the diagnostic circuitry 140 shown in FIG. 1 controls the operation of the transducer 146. In some embodiments, the spectral content of the vibration signal 200 is controlled by diagnostic circuitry 140. Diagnostic circuitry 140 can, for example, include an analog to digital converter which digitizes the signal received by receiver 146. Analog circuitry can also be employed in some embodiments. Advanced digital processing techniques can be used including performing a Fast Fourier Transform (FFT) on the received signal.

A plugged or partially plugged line condition can be detected based upon the received vibration signal. For example, a signal comprising a wide spectrum burst, or a swept signal, of acoustic noise is applied to the impulse piping 112 through noise source 144. The noise burst can be directionally coupled into the process connection 110 such that it travels along the process fluid in the impulse piping line 112. If a complete or partial interface exists in the line 112 due to plugging, a partially filled wet or dry leg, or other condition, a portion of the acoustic energy is reflected back to the receiver 146 of transducer 142. The transducer converts this received acoustic energy into an electrical signal which is provided to diagnostic circuitry 140. On the other hand, if no fault condition due to an obstruction exists, the only reflected signal will be due to fittings, bends, and normal obstructions in the line 112. These reflections are due to fixed sources. Thus, the acoustical profile of the process impulse line 112 in a nominal condition can be stored in memory 141 of diagnostic circuitry 140. During operation, the actual reflected signal can be compared with the stored profile. Variations between the stored profile and the received reflected signal are used by diagnostic circuitry 140 to identify a failure or impending failure in process line 112. Because the applied acoustic signal is known, the present invention is less susceptible to variations in the ambient noise for identifying line plugging than prior art techniques.

In some embodiments, the present invention is used to detect fault conditions in wet or dry legs of a process coupling. Wet legs are typically used in level measurement applications which are based upon differential pressure in which the top connection to a tank or other container is connected to a low pressure input of a transmitter with an impulse line that is intentionally kept filled with process fluid. However, maintenance may be required and performance can be degraded when the wet leg is only partially filled with fluid. A worst case scenario is one in which the wet leg fill level varies with time. This can lead to inaccurate measurements. A dry leg installation is similar, except that the impulse line is intentionally kept free of process fluid, i.e., the line is dry. Any fluid build up in a dry leg causes an apparent drift in the transmitter measurement. By sensing fluid levels in the wet or dry impulse lines, the present invention can detect when the levels are inappropriate and responsively provide a diagnostic output.

When an impulse line becomes plugged, the obstruction tends to act as a low pass filter. Higher frequencies of the transmitter signal are attenuated and partially reflected back to the transducer 142. The diagnostic circuitry 140 can identify a change in the spectral content of the reflected signal which can be an indication of line plugging. At a predetermined level of attenuation, for example, an early warning alarm can be communicated to a remote location by input/output circuitry 122 over process control loop 106.

In addition to detecting the reflected signal from source 144, receiver 146 can also be used to detect ambient process noise. This can be used to diagnose process conditions such as a pump failure, cavitation, etc. This can be coupled with other diagnostic techniques and used to diagnose other conditions in the process.

The vibration based diagnostics of the present invention can also be used to identify loss of isolation fluid in the process transmitter 102. As discussed above, typically isolation diaphragms are used which isolate process fluid from the sensor 114. Isolation fluid couples an isolation diaphragm to the sensor 114 such that variations in process pressure passed through the isolation diaphragm and isolation fluid oil to the process sensor. However, if the isolation fluid leaks, errors arise in sensor measurements and the sensor will ultimately fail. The oil/isolator/sensor form a low pass filter for audio signals. As fill fluid oil is lost in the transmitter, the characteristic of this low pass filter changes. The corner (i.e., frequency at which the signal is reduced by_3 dB) frequency of the low pass filter moves lower as the isolation fill fluid is lost. The transducer 142 of the present invention can be used to identify variations in this low pass filter and diagnose fill fluid loss conditions. The diagnostic circuitry 140 compares the reflected signal with a known profile to determine fill fluid loss.

Diagnostic circuitry 140 can also provide self diagnostics. For example, certain obstructions and configurations in the process impulse piping 112 provide a fixed or established time delay and amplitude of reflected pulses. Measuring the time delay and amplitudes over time, diagnostic circuitry 140 can identify a degradation or failure of the transducer 142.

The diagnostics of the present invention can be implemented using a single transducer or through multiple transducers. The diagnostic circuitry and transducer can be incorporated into transmitter electronics or can be part of a stand alone device. The transducer can couple to any type of process impulse piping including other manifold configurations. Various types of transmitters can include pressure, temperature, pH, flow, level, and other types. The diagnostic circuitry 140 can share components with other circuitry in the device, for example a microprocessor, memory, amplifier, analog to digital converter, digital to analog converter, etc. The diagnostic circuitry can be implemented in hardware, software, or their combination.

Although the present invention has been described with reference to preferred embodiments, workers skilled in the art will recognize that changes may be made in form and detail without departing from the spirit and scope of the invention. For example, the vibration signal can be of any appropriate frequency or spectral content. The signal can be applied continuously, in bursts or pulses, or in other wave forms such as a ramped signal, etc. The diagnostic circuitry can compare the received vibration signal to a reference and can identify trends or abrupt changes in the signal. Additionally, the diagnostic circuitry can monitor background noise, for example when the vibration source is off, and compare monitored ambient noise to a stored noise spectrum or signature. The comparison can provide an indication of an anomaly or pending failure of the process equipment. In some embodiments, the frequency or spectral content of the vibration signal is adjusted as desired. For example, the spectral content can be adjusted to achieve a desired signal to noise ratio. The diagnostic circuitry of the present invention can also be configured to diagnose variations, such as failure modes, in impulse piping of the type which forms a filled capillary leg of the level measurement device. In such a configuration, the transmitter provides a level measurement output. Example failures include loss of oil, a ruptured or missing process isolator, or a kinked or broken capillary leg tube.

What is claimed is:

1. A process variable transmitter for sensing a process variable of an industrial process, comprising:
   a process variable sensor configured to sense the process variable;
   an impulse piping line configured to couple the process variable sensor to a process fluid of an industrial process;
   a vibration signal source configured to transmit an acoustic vibration signal into the industrial process and through the impulse piping line, the acoustic vibration signal having an acoustic signature, the vibration signal source providing the acoustic vibration signal in response to an input;
   a vibration signal receiver acoustically coupled to the impulse piping configured to receive the vibration signal from the impulse piping line wherein the vibration signal is generated by the vibration signal source; and
   diagnostic circuitry configured to provide the input to the vibration signal source and responsively diagnose condition of the impulse piping line based upon the received vibration signal.

2. The apparatus of claim 1 wherein the diagnostic circuitry is further configured to monitor background noise.

3. The apparatus of claim 1 wherein the diagnostic circuitry compares monitored background noise with a stored reference noise signature to identify failure or pending failure of process equipment.

4. The apparatus of claim 1 wherein a frequency of the vibration signal is adjusted to change a signal to noise ratio.

5. The apparatus of claim 1 wherein the diagnostic circuitry is configured to diagnose variations in impulse piping which forms a filled capillary leg of a level measurement device.

6. The apparatus of claim 1 wherein the diagnostic circuitry includes a memory containing a spectral profile of a received vibration signal.

7. The apparatus of claim 1 wherein the diagnostic circuitry comprises comparing the received vibration signal to a reference.

8. The apparatus of claim 1 wherein the vibration signal source and signal receiver are formed by a transducer.

9. The apparatus of claim 1 wherein the vibration signal comprises a noise signal.

10. The apparatus of claim 1 wherein the vibration signal has a frequency of less than about 20 Hz.

11. The apparatus of claim 1 wherein the vibration signal source and vibration signal receiver are coupled to a process coupling.

12. The apparatus of claim 11 wherein the process coupling comprises a flange.

13. The apparatus of claim 12 wherein the vibration signal source and vibration signal receiver are inserted through and disposed within an opening in the flange.

14. The apparatus of claim 1 wherein the vibration signal source is configured to direct the transmitted vibration signal along a length of the impulse piping line.

15. The apparatus of claim 1 wherein the sensed process variable comprises flow of process fluid.

16. The apparatus of claim 1 wherein the sensed process variable comprises pressure of process fluid.

17. The apparatus of claim 1 wherein the sensed process variable comprises level of process fluid.

18. The apparatus of claim 1 includes a transmitter housing and the vibration signal source and vibration signal receiver couple to the diagnostic circuitry through an opening in the transmitter housing.

19. The apparatus of claim 1 wherein including output circuitry configured to couple to a two-wire process control loop.

20. The apparatus of claim 19 wherein circuitry is configured to be completely powered with power received from the process control loop.

21. The apparatus of claim 1 wherein the diagnostic circuitry is configured to diagnose plugging of the impulse piping line.

22. The apparatus of claim 1 wherein the diagnostic circuitry is configured to diagnose loss of fill fluid in the impulse piping line.

23. The apparatus of claim 1 wherein the diagnostic circuitry is configured to diagnose variations in impulse piping line forming a wet leg of a level measurement device.

24. The apparatus of claim 1 wherein the diagnostic circuitry is configured to diagnose variations in impulse piping line forming a dry leg of a level measurement device.

25. The apparatus of claim 1 wherein the diagnostic circuitry performs a self diagnostic based upon the received vibration signal.

26. The apparatus of claim 1 wherein the vibration signal source and vibration signal receiver comprise a piezoelectric transducer.

27. A method of sensing a process variable in an industrial process, comprising:

coupling a process variable sensor to the process fluid of the industrial process using impulse piping;

sensing a process variable of the process fluid using the process variable sensor;

controlling a vibration signal source with an input to the vibration signal source to generate a desired acoustic vibration signal having an acoustic signature response to the input and sending the vibration signal along the impulse piping;

receiving the vibration signal from the impulse piping line with a sensor acoustically coupled to the impulse piping; and diagnosing condition of the impulse piping based upon the received vibration signal.

28. The method of claim 27 wherein the diagnosing includes retrieving a spectral profile of a received vibration signal.

29. The method of claim 27 wherein the diagnosing comprises comparing the received vibration signal to a reference.

30. The method of claim 27 wherein the vibration signal comprises a noise signal.

31. The method of claim 27 wherein the vibration signal has a frequency of less than about 20 Hz.

32. The method of claim 27 including coupling the vibration signal to a process coupling.

33. The method of claim 32 wherein the process coupling comprises providing a flange.

34. The method of claim 27 wherein process variable sensor comprises a pressure sensor.

35. The method of claim 27 including directing the vibration signal along a length of the impulse piping.

36. The method of claim 27 including transmitting diagnostic data on a two-wire process control loop.

37. The method of claim 27 including diagnosing plugging of the impulse piping.

38. The method of claim 27 including diagnosing loss of fill fluid in the impulse piping.

39. The method of claim 27 including diagnosing variations in impulse piping forming a wet leg of a level measurement device.

40. The method of claim 27 including diagnosing variations in impulse piping forming a dry leg of a level measurement device.

41. The method of claim 27 including performing a self diagnostic based upon the received vibration signal.

* * * * *